(12) United States Patent
Kishima (10) Patent No.: US 9,438,848 B2
(45) Date of Patent: Sep. 6, 2016

(54) IMAGE OBTAINING APPARATUS, IMAGE OBTAINING METHOD, AND IMAGE OBTAINING PROGRAM

(71) Applicant: Sony Corporation, Tokyo (JP)

(72) Inventor: Koichiro Kishima, Kanagawa (JP)

(73) Assignee: Sony Corporation, Tokyo (JP)

( * ) Notice: Subject to any disclaimer, the term of this patent is extended or adjusted under 35 U.S.C. 154(b) by 668 days.

(21) Appl. No.: 13/672,763

(22) Filed: Nov. 9, 2012

(65) Prior Publication Data

US 2013/0128024 A1    May 23, 2013

(30) Foreign Application Priority Data

Nov. 18, 2011 (JP) .................................. 2011-252643

(51) Int. Cl.
| | |
|---|---|
| H04N 7/18 | (2006.01) |
| H04N 9/73 | (2006.01) |
| G02B 21/00 | (2006.01) |
| G01N 21/64 | (2006.01) |
| G01N 33/48 | (2006.01) |
| H04N 7/00 | (2011.01) |
| G02B 21/16 | (2006.01) |
| G02B 21/36 | (2006.01) |

(52) U.S. Cl.
CPC .......... H04N 7/002 (2013.01); G01N 21/6428 (2013.01); G01N 21/6456 (2013.01); G02B 21/16 (2013.01); G02B 21/365 (2013.01); G02B 2207/113 (2013.01)

(58) Field of Classification Search
CPC ............ H04N 7/12; H04N 9/73; H04N 7/18; G02B 21/00; G01N 21/64; C12M 1/36
See application file for complete search history.

(56) References Cited

U.S. PATENT DOCUMENTS

| | | | | |
|---|---|---|---|---|
| 4,829,374 | A * | 5/1989 | Miyamoto | ........... G02B 21/244 348/128 |
| 6,388,809 | B1 * | 5/2002 | MacAulay | ..................... 359/383 |
| 2011/0212486 | A1 * | 9/2011 | Yamada et al. | .............. 435/40.5 |
| 2011/0279703 | A1 * | 11/2011 | Lee | ............. 348/223.1 |
| 2012/0220022 | A1 * | 8/2012 | Ehrlich | ................. G01N 15/14 435/286.2 |

FOREIGN PATENT DOCUMENTS

JP          2011-107699 A      6/2011

OTHER PUBLICATIONS

Fluorescence in situ hybridization method (Fluorescence in situ hybridization: FISH); Sep. 2009.

* cited by examiner

Primary Examiner — Sath V Perungavoor
Assistant Examiner — Patricia I Young
(74) Attorney, Agent, or Firm — CHIP Law Group (57) ABSTRACT

An image obtaining apparatus includes: a light source configured to irradiate a biological sample having a fluorescent label with an excitation light, the excitation light exciting the fluorescent label; a focus moving unit configured to move a focus position of an optical system in the thickness direction of the biological sample; and a data processing unit configured to expose an image sensor to light while moving the focus position of the optical system in each of a plurality of preset scanning ranges to thereby obtain fluorescent images of the biological sample, each of the plurality of scanning ranges having a predetermined scanning length, the predetermined scanning length being smaller than the length of a bright-point detection range of the biological sample in the thickness direction, the center positions of the scanning ranges being different from each other in the thickness direction.

9 Claims, 8 Drawing Sheets

IMAGE OBTAINING APPARATUS, IMAGE OBTAINING METHOD, AND IMAGE OBTAINING PROGRAM

BACKGROUND

The present disclosure relates to an image obtaining apparatus, an image obtaining method, and an image obtaining program obtaining an image by using a microscope.

Cancer cells of some breast-cancer patients have more HER-2 receptors, a kind of protein, than normal cells do. In view of this, a surgically-resected sample is examined by the HER-2 (Human Epithelialgrowth factor Receptor type 2) examination method. Based on the result, a medicine, which will be administered to a patient after the operation, is selected. In the HER-2 examination method, a surgically-resected sample (mammary tissue) is stained with a reagent called PathVysion in HER-2 DNA probe kit. The reagent includes probes. One probe hybridizes HER-2/neu genes, which code HER-2 proteins. The other probe hybridizes alpha-satellite DNA sequences in a centromere area of chromosome 17.

When a sample is irradiated with an excitation light, which excites the probes, the probes are excited and emit fluorescence. In this case, the wavelength of the fluorescence emitted from the probe, which hybridizes HER-2/neu genes, is different from the wavelength of the fluorescence emitted from the probe, which hybridizes alpha-satellite DNA sequences. In other words, HER-2/neu genes emit red fluorescence, and alpha-satellite DNA sequences emit green fluorescence. In diagnosis, it is determined that HER-2/neu genes are increased or not based on the ratio between the number of red bright points and the number of green bright points. The red bright points are fluorescent labels showing HER-2/neu genes in a cell nucleus. The green bright points are fluorescent labels showing alpha-satellite DNA sequences in a cell nucleus. In a case where the ratio of the number of the fluorescent labels showing HER-2/neu genes to the number of the fluorescent labels showing alpha-satellite DNA sequences is equal to or more than 2.2, HER-2 positive reaction is determined (see HER-2 Examination Guide, 3rd edition, Trastuzumab Pathology Working Group, September 2009, p. 10 <FISH-method determination method>).

Further, Japanese Patent Application Laid-open No. 2011-107669 discloses a technology of detecting bright points, which mark a target cell, from a fluorescent image of a biological sample. Japanese Patent Application Laid-open No. 2011-107669 discloses a biological sample image obtaining apparatus. The biological sample image obtaining apparatus moves the focus of an objective lens in the thickness direction of a target site of a biological sample. At the same time, the biological sample image obtaining apparatus moves the image of a site magnified by the objective lens, which is formed by an image sensor, in the surface direction. The biological sample image obtaining apparatus is capable of distinguishing bright points, which are generated by fluorescent markers emitting light, from bright points, which are generated by noises. As a result, accuracy of detecting bright points may be improved.

SUMMARY

Meanwhile, the higher the numerical aperture (NA) of an optical system, the higher the brightness of bright points and the resolution of an image, which is observed by using a fluorescent microscope. Because of this, by using a microscope using an optical system whose numerical aperture (NA) is high, accuracy of the diagnosis may be increased. However, if the numerical aperture (NA) of an optical system is high, the focal depth is narrow. Because of this, the fluorescent images of bright points, which are distant from the focal depth, are blurred. As a result, images of bright points, which have various levels of brightness and various sizes, are mixed. As a result, the bright points may not be counted accurately.

In view of the above-mentioned circumstances, the following method may be employed. That is, the focus position is continuously moved, and an image is taken every time the focus position is moved. Images, each of which includes bright points in focus, are retrieved from the took images. The brightness and size of each bright point in each image are measured. However, this method requires a large-capacity memory for storing pieces of image data, the number of the pieces of image data corresponding to the number of took images. In addition, it is necessary to refer to a plurality of pieces of image data in order to pick up bright points in one cell nucleus. This method requires a number of steps, and is inefficient.

In view of the above-mentioned circumstances, it is desired to provide an image obtaining apparatus, an image obtaining method, and an image obtaining program, which may improve accuracy of detecting bright points as fluorescent labels.

According to an embodiment of the present technology, there is provided an image obtaining apparatus, including: a light source configured to irradiate a biological sample having a fluorescent label with an excitation light, the excitation light exciting the fluorescent label; an optical system including an objective lens, the objective lens being configured to magnify an imaging target of the biological sample; an image sensor configured to form an image of the imaging target magnified by the objective lens; a focus moving unit configured to move a focus position of the optical system in the thickness direction of the biological sample; and a data processing unit configured to expose the image sensor to light while moving the focus position of the optical system in each of a plurality of preset scanning ranges to thereby obtain fluorescent images of the biological sample, each of the plurality of scanning ranges having a predetermined scanning length, the predetermined scanning length being smaller than the length of a bright-point detection range of the biological sample in the thickness direction, the center positions of the scanning ranges being different from each other in the thickness direction.

In the image obtaining apparatus, it is preferable that the distance, in the thickness direction of the biological sample, between the center position of one scanning range and the center position of another scanning range next to the one scanning range be smaller than the predetermined scanning length.

In the image obtaining apparatus, the data processing unit may be configured to perform frequency analysis of the fluorescent images of the respective scanning ranges to thereby determine a fluorescent image including the most high-frequency components.

In the image obtaining apparatus, the data processing unit may be configured to count the number of bright points in each cell nucleus in the determined fluorescent image, the bright points satisfying conditions of predetermined brightness and size.

The biological sample may be a surgically-resected sample.

According to another embodiment of the present technology, there is provided an image obtaining method, including: irradiating a biological sample having a fluorescent label with an excitation light, the excitation light exciting the fluorescent label; moving the focus position of an optical system including an objective lens in each of a plurality of preset scanning ranges, each of the plurality of scanning ranges having a predetermined scanning length, the predetermined scanning length being smaller than the length of a bright-point detection range of the biological sample in the thickness direction, the center positions of the scanning ranges being different from each other in the thickness direction; and exposing an image sensor to light when the focus position is being moved in each of the scanning ranges to thereby obtain fluorescent images of the respective scanning ranges.

According to another embodiment of the present technology, there is provided an image obtaining program, configured to cause a computer to execute the steps of: irradiating a biological sample having a fluorescent label with an excitation light from a light source, the excitation light exciting the fluorescent label; moving the focus position of an optical system including an objective lens in each of a plurality of preset scanning ranges, each of the plurality of scanning ranges having a predetermined scanning length, the predetermined scanning length being smaller than the length of a bright-point detection range of the biological sample in the thickness direction, the center positions of the scanning ranges being different from each other in the thickness direction; and exposing an image sensor to light when the focus position is being moved in each of the scanning ranges to thereby obtain fluorescent images of the respective scanning ranges.

As described above, according to this technology, it is possible to improve accuracy of detecting bright points as fluorescent labels.

These and other objects, features and advantages of the present disclosure will become more apparent in light of the following detailed description of best mode embodiments thereof, as illustrated in the accompanying drawings.

DETAILED DESCRIPTION OF EMBODIMENTS

Hereinafter, an embodiment of the present disclosure will be described with reference to the drawings.

<First Embodiment>
[Structure of Image Obtaining Apparatus]

Figure 1:
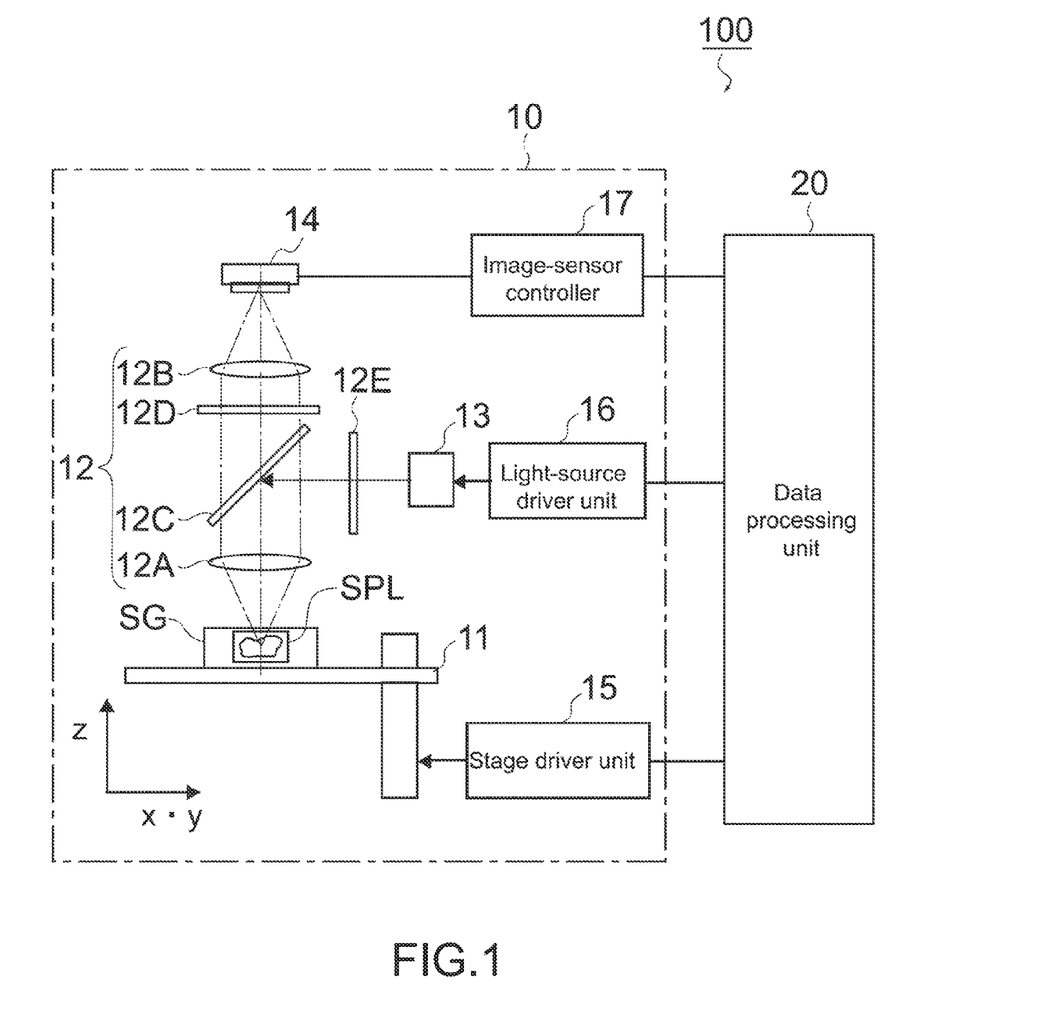
FIG. 1 is a schematic diagram showing an image obtaining apparatus according to a first embodiment of the present technology.

FIG. 1 is a schematic diagram showing an image obtaining apparatus 100 according to a first embodiment. As shown in FIG. 1, the image obtaining apparatus 100 of this embodiment includes a microscope 10 and a data processing unit 20.

[Structure of Microscope]

The microscope 10 includes a stage 11, an optical system 12, a light source 13, and an image sensor 14.

The stage 11 has a mount surface. A biological sample SPL is mounted on the mount surface. Examples of the biological sample SPL include a slice of tissue, a cell, a biopolymer such as a chromosome, and the like. The stage 11 is capable of moving in the horizontal direction (X-Y plane direction) and in the vertical direction (Z-axis direction) with respect to the mount surface. Here, the biological sample SPL is, for example, a surgically-resected sample, which is an examination target of HER-2 (Human Epithelial growth factor Receptor type 2) examination method, or another sample.

Figure 2:
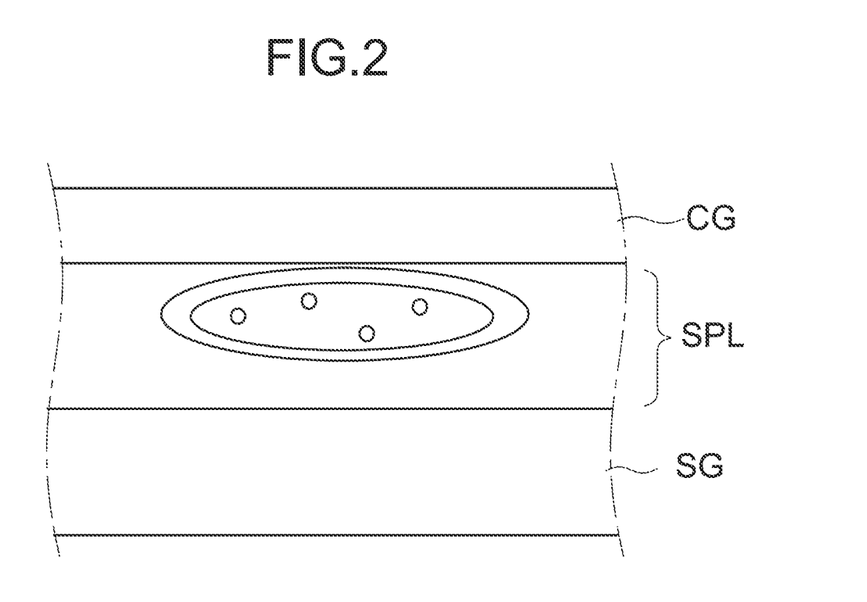
FIG. 2 is a diagram showing a biological sample as a target, whose image is to be obtained by the image obtaining apparatus of FIG. 1.

FIG. 2 is a diagram showing the biological sample SPL mounted on the above-mentioned stage 11. FIG. 2 shows the biological sample SPL in the direction from the side of the stage 11. As shown in FIG. 2, the biological sample SPL has a thickness of several μm to several tens of μm in the Z direction, for example. The biological sample SPL is sandwiched between a slide glass SG and a cover glass CG, and is fixed by a predetermined fixing method. The biological sample SPL is dyed with a fluorescence staining reagent. Fluorescence staining reagent is a stain irradiated with an excitation light from the same light source to thereby emit fluorescence. As the fluorescence staining reagent, for example, DAPI (4',6-diamidino-2-phenylindole), SpAqua, SpGreen, or the like may be used.

With reference to FIG. 1 again, the optical system 12 is arranged above the stage 11. The optical system 12 includes an objective lens 12A, an imaging lens 12B, a dichroic mirror 12C, an emission filter 12D, and an excitation filter 12E. The light source 13 is, for example, a light bulb such as a mercury lamp, an LED (Light Emitting Diode), or the like. Fluorescent labels in a biological sample are irradiated with an excitation light from the light source 13.

In a case of obtaining a fluorescent image of the biological sample SPL, the excitation filter 12E only causes light, which has an excitation wavelength for exciting fluorescent dye, to pass through, out of light emitted from the light source 13, to thereby generate an excitation light. The excitation light, which has passed through the excitation filter and enters the dichroic mirror 12C, is reflected by the dichroic mirror 12C, and is guided to the objective lens 12A. The objective lens 12A condenses the excitation light on the biological sample SPL. Then, the objective lens 12A and the imaging lens 12B magnify the image of the biological sample SPL at a predetermined power, and form the magnified image in an imaging area of the image sensor 14.

When the biological sample SPL is irradiated with the excitation light, the stain emits fluorescence. The stain is bound to each tissue of the biological sample SPL. The fluorescence passes through the dichroic mirror 12C via objective lens 12A, and reaches the imaging lens 12B via emission filter 12D. The emission filter 12D absorbs light, which is magnified by the above-mentioned the objective lens 12A and has passed through the excitation filter 12E. Only part of color light passes through the emission filter 12D. As described above, the imaging lens 12B magnifies an image of the color light, from which outside light is lost. The imaging lens 12B forms an image on the image sensor 14.

As the image sensor 14, for example, a CCD (Charge Coupled Device), a CMOS (Complementary Metal Oxide Semiconductor) image sensor, or the like is used. The image sensor 14 has a photoelectric conversion element, which receives RGB (Red, Green, Blue) colors separately and converts the colors into electric signals. The image sensor 14 is a color imager, which obtains a color image based on incident light.

The data processing unit 20 drives the light source 13. The data processing unit 20 obtains a fluorescent image of the biological sample SPL by using the image sensor 14. The data processing unit 20 stores the fluorescent image as sample data.

[Configuration of Data Processing Unit]

Figure 3:
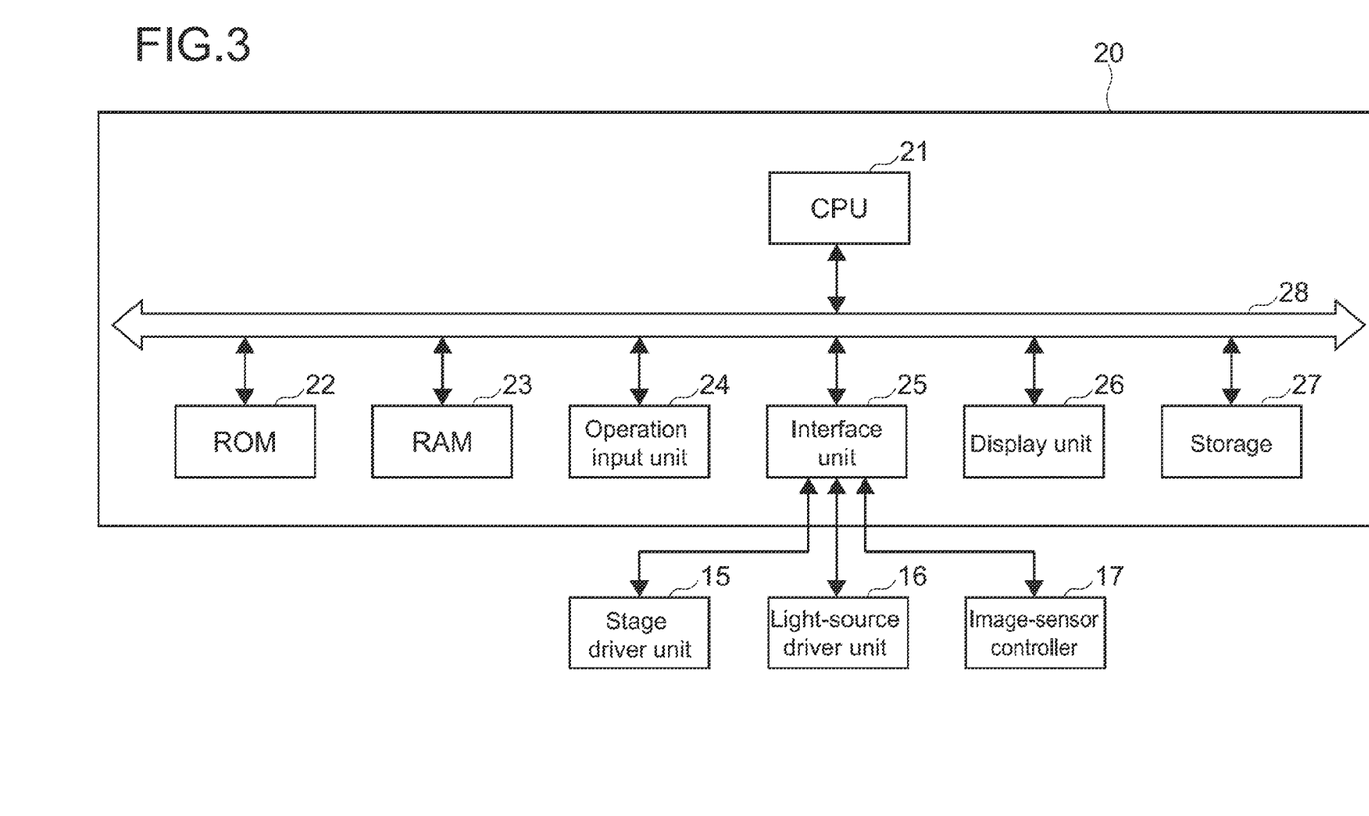
FIG. 3 is a block diagram showing a hardware configuration of a data processing unit of the image obtaining apparatus of FIG. 1.

FIG. 3 is a block diagram showing the hardware configuration of the data processing unit 20.

The data processing unit 20 is configured by, for example, a PC (Personal Computer). The data processing unit 20 stores a fluorescent image of the biological sample SPL, which is obtained from the image sensor 14, as digital image data of an arbitrary-format such as JPEG (Joint Photographic Experts Group), for example.

As shown in FIG. 3, the data processing unit 20 includes a CPU (Central Processing Unit) 21, a ROM (Read Only Memory) 22, a RAM (Random Access Memory) 23, an operation input unit 24, an interface unit 25, a display unit 26, and storage 27. Those blocks are connected to each other via a bus 28.

The ROM 22 is fixed storage for storing data and a plurality of programs such as firmware executing various processing. The RAM 23 is used as a work area of the CPU 21, and temporarily stores an OS (Operating System), various applications being executed, and various data being processed.

The storage 27 is a nonvolatile memory such as an HDD (Hard Disk Drive), a flash memory, or another solid memory, for example. The OS, various applications, and various data are stored in the storage 27. Specifically, in this embodiment, fluorescent image data captured by the image sensor 14 and an image processing application for processing fluorescent image data are stored in the storage 27.

The interface unit 25 is connected to a control board including a stage driver unit 15, a light-source driver unit 16, and an image-sensor controller 17. The stage driver unit 15 drives the stage 11 of the microscope 10. The light-source driver unit 16 drives the light source 13 of the microscope 10. The image-sensor controller 17 drives the image sensor 14 of the microscope 10. The interface unit 25 sends and receives signals to and from the control board and the data processing unit 20 according to a predetermined communication standard. Here, the stage 11 and the stage driver unit 15 serve as a focus moving unit. The focus moving unit moves the focus position of the optical system 12 in the thickness direction of a biological sample.

The CPU 21 expands, in the RAM 23, programs corresponding to instructions received from the operation input unit 24 out of a plurality of programs stored in the ROM 22 or in the storage 27. The CPU 21 arbitrarily controls the display unit 26 and the storage 27 according to the expanded programs.

The operation input unit 24 is an operating device such as a pointing device (for example, mouse), a keyboard, or a touch panel.

The display unit 26 is a liquid crystal display, an EL (Electro-Luminescence) display, a plasma display, a CRT (Cathode Ray Tube) display, or the like, for example. The display unit 26 may be built in the data processing unit 20, or may be externally connected to the data processing unit 20.

[Typical Process of Obtaining Biological Sample Fluorescent Image]

Before describing a process of obtaining a biological sample fluorescent image by the image obtaining apparatus 100 of this embodiment, a typical process of obtaining a biological sample fluorescent image and a problem thereof will be described.

Figure 4:
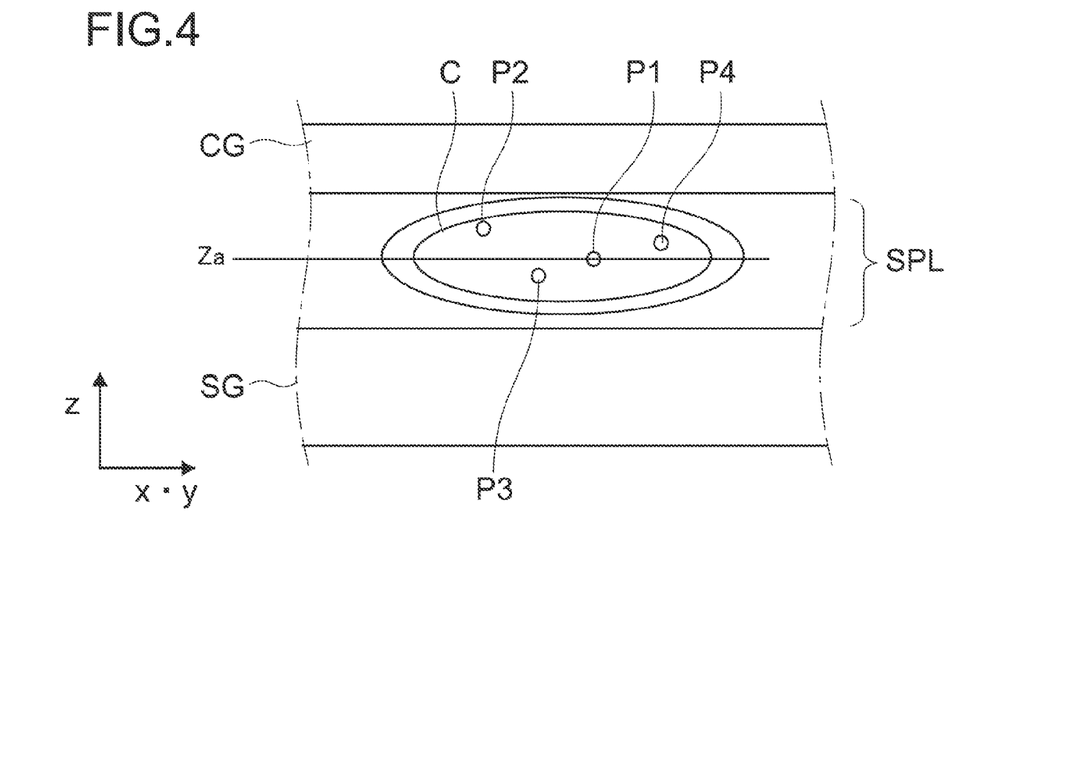
FIG. 4 is a diagram for explaining a process of obtaining a biological sample fluorescent image by a typical image obtaining apparatus.

FIG. 4 is a diagram for describing a process of obtaining a biological sample fluorescent image by a typical image obtaining apparatus.

Figure 5:
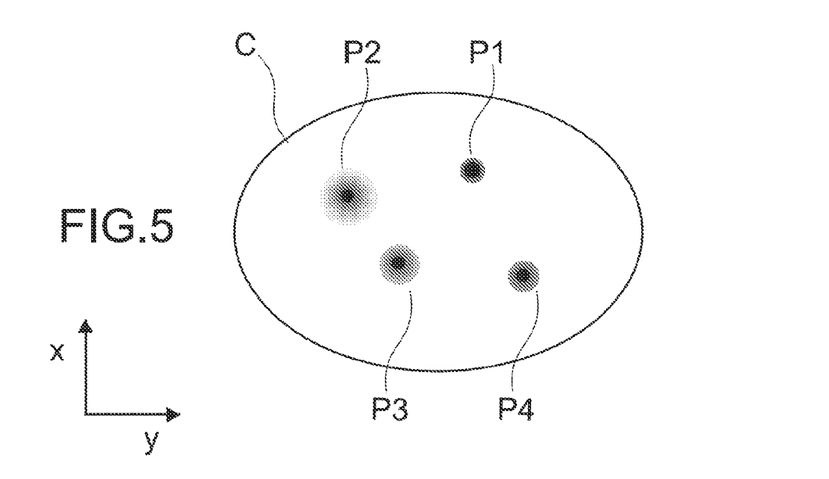
FIG. 5 is a diagram showing an example of a biological sample image obtained by a typical image obtaining apparatus.

According to this typical method, for example, the numerical aperture (NA) of an optical system is selected such that the desired resolution and brightness of bright points may be obtained. The focus position Za of the optical system is set on the middle of a biological sample SPL in the thickness (height) direction. An image of the biological sample SPL is took to thereby obtain a biological sample fluorescent image. According to this typical method, as shown in FIG. 5, the image (for example P1) of a bright point is bright and clear. This bright point exists in the vicinity of the middle position Za of the biological sample SPL in the thickness (height) direction. However, fluorescent images P2, P3, P4 are images of bright points, which are distant from the focus position Za. The fluorescent images P2, P3, P4 are blurred according to the distances from the position Za in the thickness (height) direction. It is difficult to accurately determine if conditions (brightness, size (area), and the like) of bright points are satisfied or not.

To solve the problem of accuracy, the following method may be used as another typical example. According to this method, the focus position is continuously moved by a predetermined amount, and an image is taken every time the focus position is moved. Images, each of which includes a bright point in focus, are retrieved from the took images. The brightness and size of each bright point is measured based on the image. However, this method requires a large-capacity memory for storing pieces of image data, the number of the pieces of image data corresponding to the number of took images. In addition, it is necessary to refer to a plurality of pieces of image data in order to pick up a bright point in one cell nucleus. This method requires a number of steps, and is inefficient.

According to this embodiment, the image obtaining apparatus 100 moves the focus position from one end of a bright-point detection range in the thickness direction of a biological sample by a first predetermined amount. The image obtaining apparatus 100 continuously exposes the image sensor 14 to light while moving the focus position in the above-mentioned manner. As a result, the image obtaining apparatus 100 takes an average image. Here, the movable range of the focus position during the continuous light-exposure is referred to as "scanning range". The image obtaining apparatus 100 moves the center position of the scanning range from the center position of the latest scanning range by a second predetermined amount. Then, the image obtaining apparatus 100 repeats the above-mentioned process similarly. The image obtaining apparatus 100 repeats the above-mentioned process until the end of the scanning range reaches the other end of the bright-point detection range of the biological sample. As a result, biological sample fluorescent images of a plurality of scanning ranges, which have different center positions, are obtained. Further, in the biological sample fluorescent images of the respective scanning ranges, the bright points P1-P4 in the biological sample are obtained as images blurred to some extent uniformly.

Figure 6:
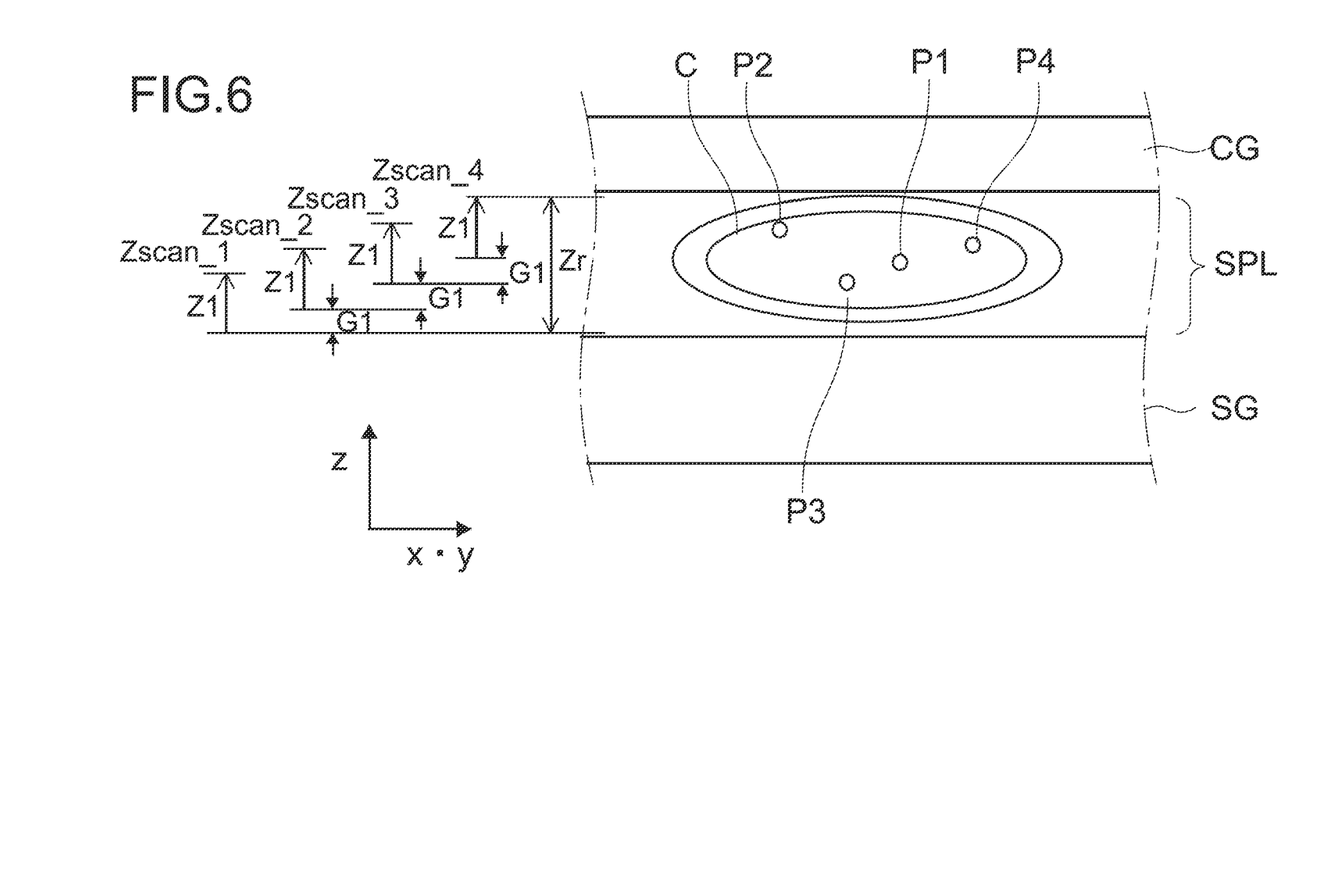
FIG. 6 is a diagram for explaining a process of obtaining a biological sample fluorescent image by the image obtaining apparatus of FIG. 1.

With reference to FIG. 6, a biological sample fluorescent image obtaining-process method according to this embodiment will be described in detail. In FIG. 6, Zr is indicative of a bright-point detection range of the biological sample SPL. Here, the bright-point detection range Zr approximately corresponds to the thickness of the biological sample SPL. However, the bright-point detection range Zr may correspond to a range, which is obtained by enlarging the thickness of the biological sample SPL in the upper and/or lower direction. Alternatively, the bright-point detection range Zr may correspond to a range, which is obtained by narrowing the thickness of the biological sample SPL in the upper and/or lower direction.

Zscan_1, Zscan_2, Zscan_3, and Zscan_4 are indicative of the scanning ranges, respectively. For example, Zscan_1, Zscan_2, Zscan_3, and Zscan_4 are scanned in this order. Alternatively, Zscan_4, Zscan_3, Zscan_2, and Zscan_1 may be scanned in this order. In this example, the number of scanning range is "4". However, according to this technology, the number of scanning range is any number larger than 1. The number of scanning range may be smaller than, equal to, or larger than 4.

The first scanning range Zscan_1 corresponds to a range from one end of the bright-point detection range Zr to a position distant from the one end by a first predetermined amount Z1 in the direction to the end of the bright-point detection range Zr. That is, the length of the scanning range is Z1. Each of all the scanning ranges Zscan_1, Zscan_2, Zscan_3, and Zscan_4 has the length Z1.

The second scanning range Zscan_2 corresponds to a range having a center position, which is distant from the center position of the first scanning range Zscan_1 by a second predetermined amount G1 in the direction to the other end of the bright-point detection range Zr.

Similarly, the third scanning range Zscan_3 corresponds to a range having a center position, which is distant from the center position of the second scanning range Zscan_2 by the second predetermined amount G1 in the direction to the other end of the bright-point detection range Zr.

Similarly, the fourth scanning range Zscan_4 corresponds to a range having a center position, which is distant from the center position of the third scanning range Zscan_3 by the second predetermined amount G1 in the direction to the other end of the bright-point detection range Zr.

Here, the second predetermined amount G1 corresponds to the distance between the center position of one scanning range and the center position of the scanning range, which is next to the one scanning range in the thickness direction (z direction) of the biological sample. The first predetermined amount Z1 corresponds to the length of each scanning range. The second predetermined amount G1 is set smaller than first predetermined amount Z1. Because of this, the plurality of obtained biological sample fluorescent images cover the entire bright-point detection range of a biological sample. The plurality of obtained biological sample fluorescent images correspond to ranges, which are obtained by dividing the bright-point detection range with higher resolution.

Note that, specifically, in a case where the bright-point detection range Zr is 6 µm for example, the first predetermined amount (scanning length) Z1 may be about 3 µm, and the second predetermined amount G1 may be 1 µm. Further, the first predetermined amount (scanning length) Z1 may be about two to four times of the focal depth of the optical system. The second predetermined amount G1 may be about one to two times of the focal depth. Note that those values may be arbitrary determined according to various conditions such as the thickness of a biological sample and the numerical aperture (NA) of an optical system. So, in the present technology, those values may not be limited to the above-mentioned values. Note that the essential condition is that the first predetermined amount (scanning length) Z1 is smaller than the bright-point detection range Zr. Further, all the second predetermined amounts G1 are not necessarily the same. For example, the distance between the center position of one scanning range and the center position of the scanning range next to the one scanning range, which are in the center portion of the bright-point detection range Zr, may be smaller than distance between the center position of one scanning range and the center position of the scanning range next to the one scanning range, which are in each end portion of the bright-point detection range Zr. As a result, the resolution in the center portion of the bright-point detection range Zr may be increased.

The image obtaining apparatus 100 continuously exposes the image sensor 14 to light for each scanning range. As a result, the image obtaining apparatus 100 obtains biological sample fluorescent images as average images for the respective scanning ranges. Then, the image obtaining apparatus 100 performs frequency analysis of the biological sample fluorescent image of each scanning range. The image obtaining apparatus 100 determines one biological sample fluorescent image, which includes the most high-frequency components, out of the plurality of biological sample fluorescent images. In other words, a biological sample fluorescent image of a scanning range, which has the largest number of bright points in focus during scanning, is a biological sample fluorescent image, which includes the most high-frequency components. Because of this, the biological sample fluorescent image of the scanning range is selected as an image, from which bright points are detected and with which the number of bright points in each cell nucleus are counted. In this situation, it is possible to accurately count the number of bright points even from one image.

[Specific Process of Obtaining Biological Sample Image by Image Obtaining Apparatus]

The CPU 21 of the data processing unit 20 expands, in the RAM 23, a program corresponding to an instruction received from the operation input unit 24 out of a plurality of programs stored in the ROM 22 or the storage 27. The CPU 21 executes the process of obtaining a biological sample fluorescent image based on the expanded program (image obtaining program).

Figure 7:
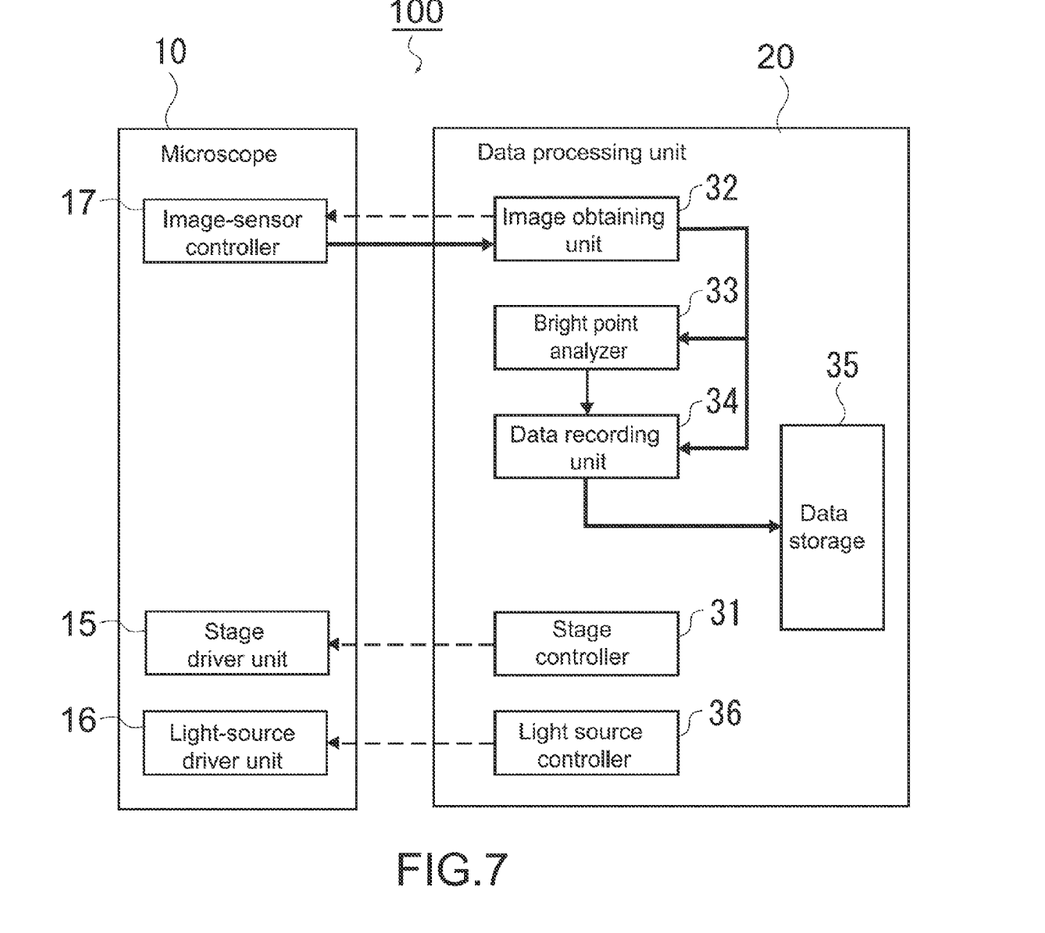
FIG. 7 is a functional block diagram showing a process of obtaining a biological sample fluorescent image by the image obtaining apparatus of FIG. 1.
Figure 8:
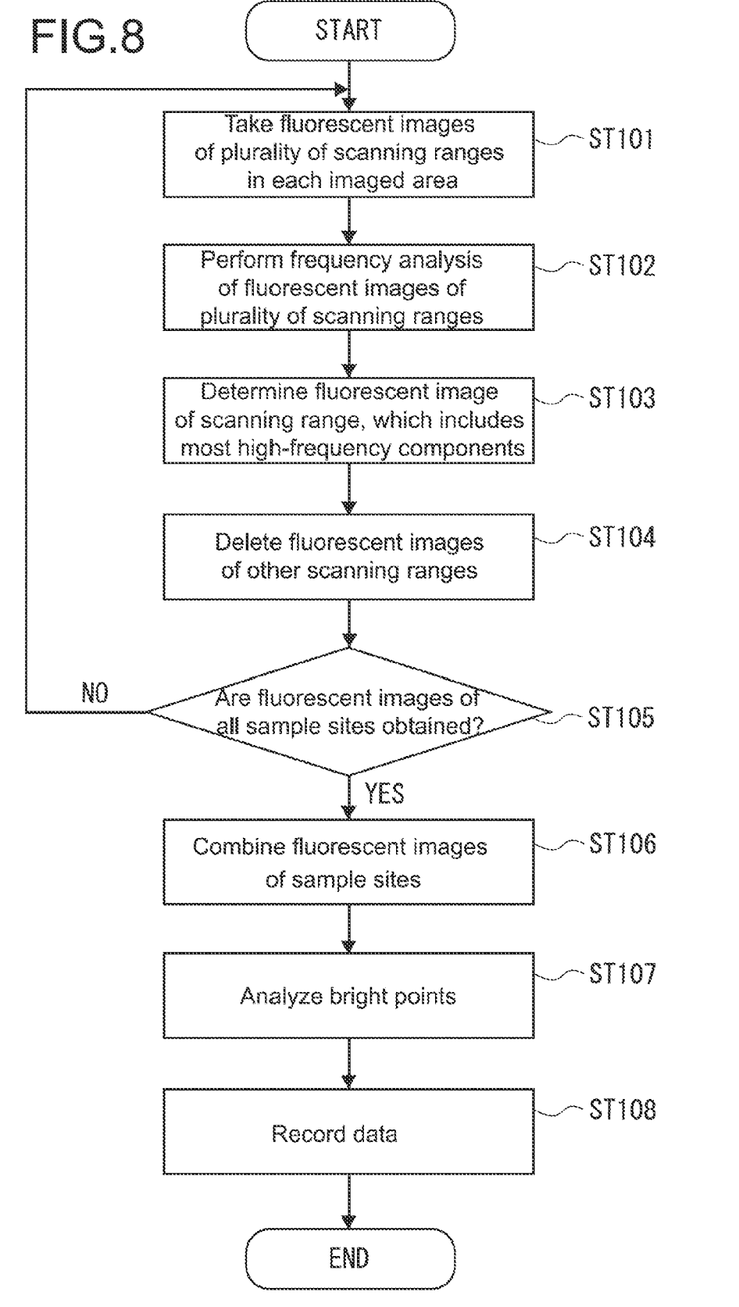
FIG. 8 is a flowchart showing a process of obtaining a biological sample fluorescent image by an image obtaining apparatus of FIG. 1.

FIG. 7 is a functional block diagram for the process of obtaining a biological sample fluorescent image. FIG. 8 is a flowchart showing the process of obtaining a biological sample fluorescent image.

Figure 9:
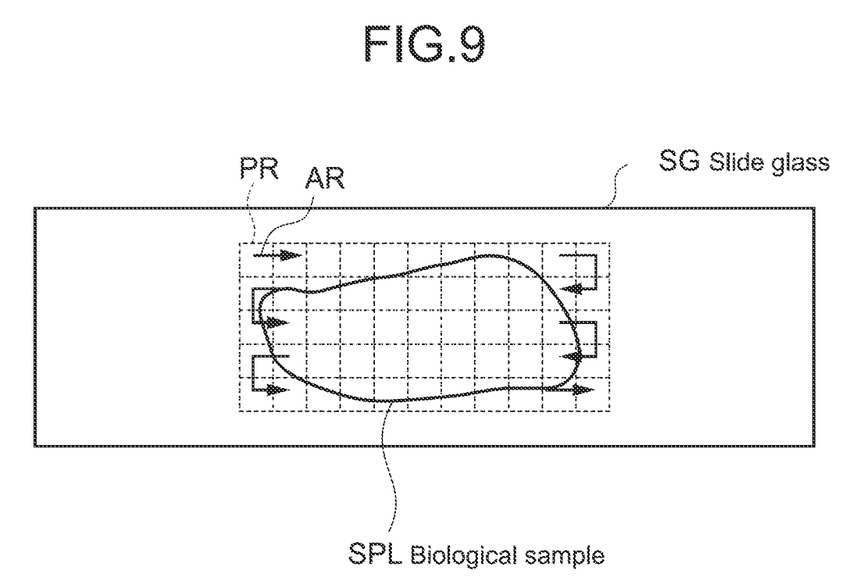
FIG. 9 is a diagram showing imaging target areas imaged by the image obtaining apparatus of FIG. 1.

A stage controller 31 sequentially moves the stage 11 such that a target site of the biological sample SPL (hereinafter, this is also referred to as "sample site") is in an imaged area. For example, as shown in FIG. 9, the stage controller 31

(movement controller) allocates the biological sample SPL to the imaged areas AR. Note that, in FIG. 9, areas of the biological sample SPL to be allocated to the imaged areas AR are not overlapped with each other. Alternatively, part of an area may be overlapped with part of an adjacent area.

First, in Step S101 (see FIG. 8), biological sample fluorescent images of a plurality of scanning ranges of each sample site in the imaged area are taken. That is, as shown in FIG. 6, the stage controller 31 moves the stage 11 in the z-axis direction (optical-axis direction of objective lens 12A) for each scanning range.

Meanwhile, an image obtaining unit 32 sends instructions to the image-sensor controller 17 to expose the image sensor 14 to light for each of the above-mentioned scanning ranges. The image sensor 14 is exposed to light for each of the above-mentioned scanning ranges, whereby fluorescent images of the sample sites are obtained. The image obtaining unit 32 obtains the fluorescent images from the image sensor 14 via image-sensor controller 17. As a result, biological sample fluorescent images of the plurality of scanning ranges are obtained for each sample sites in the imaged area (Step S101).

Subsequently, in Step S102, the image obtaining unit 32 performs frequency analysis of the obtained fluorescent image of a sample site in each scanning range (Step S102). The image obtaining unit 32 determines a fluorescent image of a sample site, which includes the most high-frequency components, out of the fluorescent images of the sample site in the respective scanning ranges (Step S103). After that, the image obtaining unit 32 deletes the fluorescent images other than the fluorescent image, which the image obtaining unit 32 determined as a fluorescent image of a sample site including the most high-frequency components, out of the fluorescent images of the sample site in the respective scanning ranges (Step S104).

The above-mentioned operations are repeated for all the sample sites.

The image obtaining unit 32 determines a fluorescent image of a sample site in a scanning range, which includes the most above-mentioned predetermined-frequency components, for each of all the sample sites (Step S105, YES). Then, the image obtaining unit 32 combines the fluorescent images of the sample sites by using a predetermined combining algorithm, to thereby generate an entire biological sample fluorescent image (Step S106). As a result, one biological sample fluorescent image is obtained. The biological sample fluorescent image is the most preferable to measure the brightness and sizes (areas) of fluorescent images of bright points.

Subsequently, the bright point analyzer 33 analyzes the bright points (Step S107). That is, the bright point analyzer 33 detects cell nuclei (C of FIG. 6) from a biological sample fluorescent image generated by the image obtaining unit 32. The cell nuclei are areas next to pixels, each of which corresponds to the nucleus marker color set as a color of cell nuclei, and has the brightness equal to or more than a threshold. Subsequently, the bright point analyzer 33 detects bright points (P1-P4 of FIG. 6) as target markers and control markers in the detected cell nuclei. That is, the bright point analyzer 33 detects, as target markers, areas (bright points) satisfying the following condition. That is, the predetermined number (areas) or more of pixels, which exhibit the marker color set for the target markers and have the brightness equal to or more than a threshold, are next to each other to thereby form an approximately-circular shape. Similarly, the bright point analyzer 33 detects, as control markers, areas (bright points) satisfying the following condition. That is, the predetermined number (areas) or more of pixels, which exhibit the marker color set for the control markers and have the brightness equal to or more than a threshold, are next to each other to thereby form an approximately-circular shape.

Then, the bright point analyzer 33 counts the number of the detected target markers and the number of the detected control markers for each cell nucleus. The bright point analyzer 33 supplies the number of the target markers and the number of the control markers to the data recording unit 34 as results of analyzing the bright points.

Meanwhile, the data recording unit 34 encodes the biological sample fluorescent image, which is obtained by combining biological sample fluorescent images of the respective sample sites by the image obtaining unit 32, to thereby obtain sample data of the predetermined compression format such as JPEG (Joint Photographic Experts Group). The data recording unit 34 records the sample data in data storage 35. The data recording unit 34 receives the results of analyzing the bright points from the bright point analyzer 33. Then, the data recording unit 34 records the analysis-result data in the data storage 35 in association with the sample data (Step S107).

As described above, the image obtaining apparatus 100 of this embodiment continuously exposes the image sensor 14 to light for each scanning range. As a result, the image obtaining apparatus 100 obtains biological sample fluorescent images as average images of the respective scanning ranges of the biological sample SPL. The image obtaining apparatus 100 performs frequency analyses of the respective biological sample fluorescent images. The image obtaining apparatus 100 determines one biological sample fluorescent image, which includes the most high-frequency components, out of a plurality of biological sample fluorescent images. In other words, the image obtaining apparatus 100 determines the biological sample fluorescent image of one scanning range, which has the largest number of bright-point images in focus during scanning. The image obtaining apparatus 100 uses the biological sample fluorescent image to analyze bright points. As a result, the image obtaining apparatus 100 is capable of accurately detecting bright points even from only one image. The image obtaining apparatus 100 is capable of accurately count the number of bright points in cell nuclei. Further, it is possible to reduce the capacity of the memory, which stores a biological sample fluorescent image as a bright-point analysis target.

Note that, in the structure of the microscope 10 of the above-mentioned embodiment, the objective lens 12A may be an eyepiece lens.

Further, in the above-mentioned embodiment, the stage 11 is moved to thereby move the focus position. Alternatively, the objective lens 12A of the optical system 12 may be moved.

In the above-mentioned embodiment, the data processing unit 20 includes the data storage 35. Biological sample images and detected results of fluorescent markers are recorded in the data storage 35. Alternatively, they may be recorded in external storage.

The microscope 10 may be connected to the data processing unit 20 not by a bus transmission path, but by a wired or wireless transmission medium such as a local area network, the Internet, or digital satellite broadcasting.

Note that the present technology may employ the following configurations.

(1) An image obtaining apparatus, comprising:
a light source configured to irradiate a biological sample having a fluorescent label with an excitation light, the excitation light exciting the fluorescent label;
an optical system including an objective lens, the objective lens being configured to magnify an imaging target of the biological sample;
an image sensor configured to form an image of the imaging target magnified by the objective lens;
a focus moving unit configured to move a focus position of the optical system in the thickness direction of the biological sample; and
a data processing unit configured to expose the image sensor to light while moving the focus position of the optical system in each of a plurality of preset scanning ranges to thereby obtain fluorescent images of the biological sample, each of the plurality of scanning ranges having a predetermined scanning length, the predetermined scanning length being smaller than the length of a bright-point detection range of the biological sample in the thickness direction, the center positions of the scanning ranges being different from each other in the thickness direction.

(2) The image obtaining apparatus according to (1), wherein
the distance, in the thickness direction of the biological sample, between the center position of one scanning range and the center position of another scanning range next to the one scanning range is smaller than the predetermined scanning length.

(3) The image obtaining apparatus according to (1) or (2), wherein
the data processing unit is configured to perform frequency analysis of the fluorescent images of the respective scanning ranges to thereby determine a fluorescent image including the most high-frequency components.

(4) The image obtaining apparatus according to any one of (1) to (3), wherein
the data processing unit is configured to count the number of bright points in each cell nucleus in the determined fluorescent image, the bright points satisfying conditions of predetermined brightness and size.

(5) The image obtaining apparatus according to any one of (1) to (4), wherein
the biological sample is a surgically-resected sample.

The present disclosure contains subject matter related to that disclosed in Japanese Priority Patent Application JP 2011-252643 filed in the Japan Patent Office on Nov. 18, 2011, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. An image obtaining apparatus, comprising:
a stage adapted to support a biological sample mounted on a mount surface of the stage, the biological sample having a fluorescent label;
a light source configured to irradiate the biological sample with an excitation light, so as to excite the fluorescent label;
an optical system including an objective lens, the objective lens being configured to magnify an imaging target of the biological sample;
an image sensor configured to form an image of the imaging target magnified by the objective lens; and
control circuitry;
wherein the stage and the objective lens are configured and arranged so that a distance between the stage and the objective lens can be adjusted so as to move a focus position of the optical system in a thickness direction of the biological sample in response to a signal; and
wherein the control circuitry is configured to control the image obtaining apparatus so as to expose the image sensor to light from the light source while generating the signal that causes the focus position of the optical system to be moved in each of a plurality of preset scanning ranges to thereby obtain fluorescent images of the biological sample, each of the plurality of scanning ranges having a predetermined scanning length, the predetermined scanning length being smaller than the length of a bright-point detection range of the biological sample in the thickness direction, the center positions of the scanning ranges being different from each other in the thickness direction.

2. The image obtaining apparatus according to claim 1, wherein
the distance, in the thickness direction of the biological sample, between the center position of one scanning range and the center position of another scanning range next to the one scanning range is smaller than the predetermined scanning length.

3. The image obtaining apparatus according to claim 2, wherein
the control circuitry is further configured to perform frequency analysis of the fluorescent images of the respective scanning ranges to thereby determine a fluorescent image including the most high-frequency components.

4. The image obtaining apparatus according to claim 3, wherein
the control circuitry is further configured to count the number of bright points in each cell nucleus in the determined fluorescent image, the bright points satisfying conditions of predetermined brightness and size.

5. An image obtaining method, comprising:
irradiating a biological sample having a fluorescent label with an excitation light, the biological sample being supported by a stage and the excitation light exciting the fluorescent label, wherein the biological sample is mounted on a mount surface of the stage;
moving the focus position of an optical system including an objective lens in each of a plurality of preset scanning ranges by adjusting a distance between the objective lens and the stage, each of the plurality of scanning ranges having a predetermined scanning length, the predetermined scanning length being smaller than the length of a bright-point detection range of the biological sample in the thickness direction, the center positions of the scanning ranges being different from each other in the thickness direction; and
exposing an image sensor to light when the focus position is being moved in each of the scanning ranges to thereby obtain fluorescent images of the respective scanning ranges.

6. A non-transitory computer readable medium having instructions which, when executed by a computer, cause the computer to control an image obtaining apparatus to:
irradiate a biological sample having a fluorescent label with an excitation light from a light source, the biological sample being supported by a stage and the excitation light exciting the fluorescent label, wherein the biological sample is mounted on a mount surface of the stage;

move the focus position of an optical system including an objective lens in each of a plurality of preset scanning ranges by adjusting a distance between the objective lens and the stage, each of the plurality of scanning ranges having a predetermined scanning length, the predetermined scanning length being smaller than the length of a bright-point detection range of the biological sample in the thickness direction, the center positions of the scanning ranges being different from each other in the thickness direction; and expose an image sensor to light when the focus position is being moved in each of the scanning ranges to thereby obtain fluorescent images of the respective scanning ranges.

7. The image obtaining apparatus according to claim 1, wherein the control circuitry comprises a central processing unit.

8. The image obtaining apparatus according to claim 1, further comprising a stage driver configured to move the stage relative to the objective lens in response to the signal.

9. The image obtaining apparatus according to claim 1, wherein the predetermined scanning length is about 3 µm and the bright-point detection range is about 6 µm.

* * * * *